(12) United States Patent
Beckmann et al.

(10) Patent No.: US 7,432,407 B2
(45) Date of Patent: Oct. 7, 2008

(54) HYDROISOMERIZATION OF OLEFINS COMPRISING BETWEEN 4 AND 6 CARBON ATOMS

(75) Inventors: Andreas Beckmann, Recklinghausen (DE); Armin Rix, Marl (DE); Udo Knippenberg, Marl (DE); Franz Nierlich, Marl (DE); Wilfried Bueschken, Haltern (DE); Ralf Duessel, Waterford, NY (US)

(73) Assignee: OXENO Olefinchemie GmbH, Marl (DE)

( * ) Notice: Subject to any disclaimer, the term of this patent is extended or adjusted under 35 U.S.C. 154(b) by 569 days.

(21) Appl. No.: 10/487,950

(22) PCT Filed: Sep. 20, 2002

(86) PCT No.: PCT/EP02/10571

§ 371 (c)(1),
(2), (4) Date: Mar. 5, 2004

(87) PCT Pub. No.: WO03/035587

PCT Pub. Date: May 1, 2003

(65) Prior Publication Data

US 2004/0210098 A1 Oct. 21, 2004

(30) Foreign Application Priority Data

Oct. 25, 2001 (DE) .............................. 101 52 842

(51) Int. Cl.
*C07C 5/25* (2006.01)
*C07C 5/08* (2006.01)
*C07C 5/05* (2006.01)

(52) U.S. Cl. ........................ 585/670; 585/259

(58) Field of Classification Search ................. 585/670, 585/259
See application file for complete search history.

(56) References Cited

U.S. PATENT DOCUMENTS

| 3,531,545 | A |   | 9/1970 | Garner et al. |
| 3,749,752 | A |   | 7/1973 | Mitsche et al. |
| 3,865,894 | A | * | 2/1975 | Kirsch et al. ................ 585/722 |
| 5,998,685 | A | * | 12/1999 | Nierlich et al. ............. 585/329 |

FOREIGN PATENT DOCUMENTS

| DE | 2728218 | 1/1978 |
| DE | 19957173 | 5/2001 |

OTHER PUBLICATIONS

U.S. Appl. No. 10/790,706, filed Mar. 3, 2004, Beckmann, et al.
U.S. Appl. No. 10/805,256, filed Mar. 22, 2004, Beckmann, et al.
U.S. Appl. No. 10/790,707, filed Mar. 3, 2004, Beckmann, et al.
U.S. Appl. No. 10/467,844, filed Aug. 13, 2003, Nierlich, et al.
U.S. Appl. No. 10/634,894, filed Aug. 6, 2003, Beckmann, et al.
U.S. Appl. No. 10/739,086, filed Dec. 19, 2003, Scholz, et al.
U.S. Appl. No. 10/868,904, filed Jun. 17, 2004, Beckmann, et al.
U.S. Appl. No. 10/893,306, filed Jul. 19, 2004, Fernandez, et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

The invention relates to a process by which $C_4$- to $C_6$-olefins or an essentially sulfur-free olefin cut comprising $C_4$- to $C_6$-olefins is isomerized over a catalyst comprising an element of the eighth transition group of the Periodic Table, in the presence of at least one added sulfur compound, and any polyunsaturated hydrocarbons contained therein are selectively hydrogenated and hydroisomerized, and also the sulfur compounds are separated from the product and optionally recycled, so that virtually sulfur-free products are obtained.

18 Claims, 2 Drawing Sheets ns having internal double bonds. The isomerization comprises a shift of the olefinic double bonds and of hydrogen atoms with retention of the carbon skeleton and is hereafter referred to for short as hydroisomerization.

HYDROISOMERIZATION OF OLEFINS COMPRISING BETWEEN 4 AND 6 CARBON ATOMS

The invention relates to a process for isomerization of monoolefins having from 4 to 6 carbon atoms and terminal double bonds α-olefins) to give the corresponding monoolefins having internal double bonds. Any polyunsaturated hydrocarbons present are very selectively hydrogenated to monoolefins and isomerized to the corresponding monoolefins having internal double bonds. The isomerization comprises a shift of the olefinic double bonds and of hydrogen atoms with retention of the carbon skeleton and is hereafter referred to for short as hydroisomerization.

The invention further relates to the use of the monoolefins prepared by the hydroisomerization of the invention, in particular for the preparation of higher oligomers and for the preparation of gasoline alkylate.

Hydroisomerization is an important process step during the processing of $C_4$-$C_6$-olefinic mixtures when olefins having predominantly internal double bonds are intended to be the main products. For instance, $C_4$-olefinic mixtures are processed in different ways depending on the desired target products. The first step, which is common to all processing variants, is the removal of the majority of the butadiene. If butadiene can be viably marketed or there is an internal demand for it, it is separated off by extraction or extractive distillation. Otherwise, it is selectively hydrogenated to give linear butenes so that a residual concentration of not more than about 2000 ppm is present. In both cases, a hydrocarbon mixture (known as raffinate I or hydrogenated crack-$C_4$) remains, which as well as the saturated hydrocarbons n-butane and isobutane comprises the olefins isobutene, 1-butene and 2-butene (cis and trans). If 1-butene is one of the target products, further processing is carried out as follows: isobutene is removed from raffinate I or hydrogenated crack-$C_4$ by chemical reaction. The industrially most important process is the reaction of isobutene with methanol to give methyl tert-butyl ether (MTBE), which among other uses finds significant use as a motor fuel additive. Other possibilities are the conversion of isobutene to give tertiary butanol (TBA) or the acid-catalyzed oligomerization of isobutene to give diisobutene and higher oligomers. The remaining butadiene quantities are removed by a selective hydrogenation process (SHP) from the remaining isobutene-free $C_4$-cut (known as raffinate II), which comprises the linear olefins and saturated hydrocarbons, so that a concentration of less than 5 ppm remains. 1-Butene and isobutane are completely or partially removed from this mixture by distillation. The remaining mixture of linear butenes and saturated hydrocarbons can be oligomerized, for example by the Octol process, from which di-n-butene is formed as the main product.

However, if the preparation of isobutene and 2-butene, or a mixture of linear butenes having a high 2-butene content, is the target, the following course of processing is preferred: $C_4$-streams, which typically comprise not more than 1% of butadiene ($C_4$-stream from the FCC (fluid catalytic cracker), raffinate I or hydrogenated crack-$C_4$), are hydrogenated and hydroisomerized, i.e., (still) remaining butadiene is selectively hydrogenated so that a content of not more than 5 ppm remains and 1-butene is simultaneously isomerized to give 2-butenes. The equilibrium location between 1-butene and both 2-butenes together is, for example, about 1:17 at 80° C., i.e. strongly on the side of the 2-butenes. Only a mixture of isobutene, 1-butene and isobutane can be isolated as a top product from the hydroisomerization mixture, owing to the small boiling point differences, and this top product can be processed by customary methods. An isobutene-free mixture is obtained as the bottom product. This mixture is a highly suitable reactant for the preparation of oligomers, preferably of $C_8$-olefins and in particular di-n-butene.

For the oligomerization, there are in principle three process variants. Oligomerization over acid catalysts, for example zeolites or phosphoric acid on supports in industrial processes, has been known for a long time. This gives isomer mixtures of branched olefins, predominantly dimethylhexenes (WO 92/13818). A process which is also practiced worldwide is oligomerization using soluble nickel complexes, known as the DIMERSOL process (B. Cornils, W. A. Herrmann, Applied Homogenous Catalysis with Organometallic Compounds, pages 261 to 263, Verlag Chemie 1996). Finally, oligomerization over nickel fixed bed catalysts should be mentioned, such as the process of OXENO GmbH. The process is described in the literature as the OCTOL process (Hydrocarbon Process., Int. Ed. (1986) 65 (2. Sect. 1), pages 31 to 33).

The dibutenes obtained in this way are desirable feedstocks in the chemical industry. For example, hydroformylation can give rise to aldehydes which are longer by one carbon atom—in the case of dibutenes $C_9$-aldehydes—which themselves can find use for important industrial products. Examples include the hydrogenation of aldehydes to give alcohols and their reaction with carboxylic acids or carboxylic anhydrides to give esters. For instance, esterification of the alcohols with phthalic anhydride gives diisononyl phthalates, which are very desirable plasticizers in the plastics processing industry. Further, the oxidation of aldehydes to give the corresponding carboxylic acids, which can be converted to oil-soluble metal salts inter alia, is industrially important and practiced. These are used, for example, as siccatives for coatings or as stabilizers for polyvinyl chloride.

A further example of industrial use is the reaction of olefins (dibutenes) with carbon monoxide and water to give carboxylic acids which are longer by one carbon atom by using strong acids in combination as catalysts, which is described in the literature as the KOCH reaction. Tertiary branched carboxylic acid mixtures are obtained, which by their branched nature are in turn very well suited for the preparation of the previously mentioned metal salts. A particularly important use of tertiary carboxylic acids is the reaction of acetylene to give vinyl esters, which serve as comonomers for internal plasticizing of polymers. Copolymers of vinyl esters of tertiary carboxylic acids with vinyl acetate are, for example, the basis of water-dispersible environmentally friendly paints and coatings and of energy-saving insulating plasters for buildings.

The higher oligomers formed during oligomerization are also used for chemical syntheses. For example, a mixture of isomeric $C_{13}$-alcohols is obtained from tributene by hydroformylation and subsequent hydrogenation, which finds use as a precursor for the preparation of detergents and plasticizers. Hydrocarboxylation results in the formation of tertiary $C_{13}$-carboxylic acids, which can be used for similar applications to the corresponding $C_9$-carboxylic acids.

The remaining gas from the oligomerization consists of n-butane and small quantities of butenes, which are removed by hydrogenation. The highly pure n-butane is used, for example, as propellant in the production of aerosols.

The difficulty with the hydrogenation and hydroisomerization of olefin mixtures is to control the hydrogenation such that the polyunsaturated olefins, which are only present in low concentrations, are converted to the corresponding monoolefins, but the monoolefins present in high concentrations are not hydrogenated to give saturated hydrocarbons.

In the particular case of the hydrogenation and hydroisomerization of $C_4$-olefin mixtures, this means that butadiene has to be hydrogenated without losses of butenes while simultaneously isomerizing the linear butenes.

U.S. Pat. No. 4,849,576 describes a process for isomerizing of olefins, in particular of n-butenes, in a feed comprising small quantities of sulfur compounds. The isomerization is carried out over a $Pd/Al_2O_3$ catalyst in the presence of hydrogen. In order to improve the lifetime of the catalyst, a catalytic guard bed material ($SnO_2$ on $Al_2O_3$) is employed, as a pretreatment to remove at least a portion of said sulfur compounds. No information is given in this reference about the hydrogenation of dienes, which are possibly present in the feed. It is also not disclosed in this reference whether olefins are hydrogenated to saturated hydrocarbons.

U.S. Pat. No. 3,531,545 describes the isomerization of olefins over a palladium catalyst in the presence of hydrogen and sulfur compounds. Dienes, polyolefins and acetylene derivatives should be removed from the isomerization, since they interfere with the process (column 1, lines 49-57).

The two processes mentioned are therefore exclusively isomerization processes without selective hydrogenation of the polyunsaturated hydrocarbons.

Processes for the removal of sulfur compounds and dienes from $C_3$-$C_{12}$-petroleum fractions with simultaneous isomerization of the olefins present and recovery of a $C_3$-$C_5$- or $C_4$-$C_5$-cut are disclosed by Hearn et al. in U.S. Pat. No. 5,510,568, U.S. Pat. No. 5,595,634 and WO 98/12158. According to U.S. Pat. No. 5,510,568, the processing is carried out in a column reactor, which contains a palladium catalyst, in the presence of hydrogen. This gives $C_3$-$C_5$-cuts which still contain dienes. The diene content in Example 1 is 10 ppm and in Example 2 50 ppm. According to U.S. Pat. No. 5,595,634, $H_2S$ and $C_3$-hydrocarbons are separated off as overheads in an upstream column. The bottom product is fed into a column reactor with hydrogen. In this column, a nickel catalyst and a palladium catalyst are installed in separate beds. The nickel catalyst is located in the bed installed lower in the column. The addition of mercaptans present in the reactant to olefinic double bonds takes place mainly over the nickel catalyst, isomerization and selective hydrogenation predominantly over the palladium catalyst. A $C_4$-$C_5$-cut is obtained as a top product. The diene content is 46 ppm according to both examples. According to WO 98/12158, the reactant is first passed through an upstream reactor containing an $Ni/Al_2O_3$ catalyst, in which a portion of the mercaptans add onto dienes. The reactor effluent is passed together with hydrogen into a column reactor containing $Pd/Al_2O_3$ catalyst. A $C_3$-$C_5$-fraction is obtained as a top product which is neither diene-nor mercaptan-free. Contents of these compounds are not disclosed, and there is only a vague report of reduced diene and mercaptan contents compared to the reactant.

U.S. Pat. No. 5,759,386 describes processing of a light petroleum fraction which comprises small quantities of dienes (about 0.6% in Example 1) and sulfur compounds (10 to 350 ppm S). In the first step, the reactant is reacted over a nickel catalyst in the presence of hydrogen. Mercaptans are converted to thioethers, excess dienes are selectively hydrogenated and olefins are isomerized. The reactor effluent is separated into a top fraction, which comprises $C_3$-$C_5$-hydrocarbons, and a bottom fraction comprising the higher-boiling materials. The low-boiler fraction obtained in this process is again not free from dienes or sulfur compounds. A thioether content of 118 ppm and a diene content of 75 ppm are reported for Example 1.

EP-A-0 556 025 discloses a process for the removal of dienes from a light petroleum fraction (for example comprising 5% $C_4$-, 69% $C_5$- and 25.6% $C_6$-hydrocarbons) and simultaneous isomerization of the monoolefins. In this process, light petroleum is passed together with hydrogen into a distillation column which contains a $Pd/Al_2O_3$ catalyst. Hydrogen and low-boilers (0.5 to 1% of the reactant) are obtained as the top product. The bottom product has a remaining diene content of 40 ppm. The loss of monoenes is 1.9%.

GB 1 110 826 describes the isomerization of 1-butene to give 2-butenes with simultaneous removal of butadiene (less than 5% in the reactant) by selective hydrogenation to give linear butenes. A supported sulfurized nickel catalyst (Ni on sepiolite) is used. At 100° C., a 2-butene:1-butene ratio of 10.6:1 is obtained, i.e. a ratio far removed from the thermodynamic equilibrium of about 16:1.

U.S. Pat. No. 4,132,745 discloses a process for isomerization of 1-butene to give 2-butenes with simultaneous hydrogenation of small butadiene quantities present in the reactant. A sulfurized palladium catalyst is used. The disadvantages of this process are that some of the olefins are lost by over-hydrogenation to give butane and no more than 10 ppm of sulfur in the reactant can be tolerated. Furthermore, the product mixture comprises sulfur compounds.

EP-A-0 636 677 also describes the use of a sulfurized $Pd/Al_2O_3$ catalyst for the isomerization of linear butenes and for the removal of small butadiene quantities. Although the dienes are hydrogenated, the thermodynamic equilibrium of linear butenes is by no means achieved.

EP-A-0 288 362 describes processes for the hydrogenation and hydroisomerization of $C_4$-cuts which comprise 20 ppm of sulfur. The conversion takes place over two successive catalysts. The first catalyst comprises palladium as the active component and at least one further metal, which can be gold and/or platinum. The second catalyst comprises palladium. The conversion can take place in pure hydrogen or using hydrogen having a content of up to 10 000 ppm of hydrogen sulfide. A disadvantage of this process is that according to the examples where virtually complete butadiene conversion is achieved, only 80% of the theoretical quantity of 1-butene is isomerized to give 2-butene. Furthermore, the resulting products contain sulfur. A method for the removal of the sulfur compounds is not suggested.

In existing processes, the activity of the catalysts employed is moderated by sulfur compounds in the reactant. Therefore, they are particularly suitable for hydroisomerization of sulfur-rich hydrocarbon streams. However, these processes have the disadvantage that they deliver sulfur-containing products. Furthermore, the remaining diene contents and the losses of monoolefins by over-hydrogenation are frequently relatively high. Also, the thermodynamic equilibrium between olefins having terminal and internal double bonds is not always achieved.

It is an object of the present invention to provide a hydroisomerization process for $C_4$-$C_6$-olefins which simultaneously and selectively hydrogenates up to 5% of polyunsaturated hydrocarbons to monoolefins, does not have the disadvantages described above and is suitable for the conversion of preferably low-sulfur reactants to give virtually sulfur-free products which can in particular be used for oligomerization or are suitable for the production of gasoline alkylate.

This object is achieved according to the invention on hydroisomerizing $C_4$- to $C_6$-olefins or an olefinic cut comprising $C_4$- to $C_6$-olefins over a catalyst comprising an element of the eighth transition group of the Periodic Table, in the presence of at least one added sulfur compound which contains at least 4 carbon atoms and is easily removable or by hydroisomerizing and hydrogenating a mixture of $C_4$- to $C_6$-olefins comprising up to 5%, preferably up to 2% of polyunsaturated hydrocarbons contained therein in the presence of at least one added sulfur compound which fulfills the above conditions and separating the sulfur compounds from the product and optionally feeding them back into the reactant.

The invention therefore provides a process for the preparation of $C_4$- to $C_6$-olefins or of a mixture of $C_4$- to $C_6$-olefins having predominantly internal double bonds from a $C_4$- to $C_6$-olefin or a $C_4$- to $C_6$-olefin cut with or without up to 5%, preferably up to 2%, of polyunsaturated hydrocarbons, which comprises the following steps:
a) hydrogenation of any polyunsaturated hydrocarbons present using hydrogen such that a concentration of not more than 5 ppm remains
b) isomerization of olefins having terminal double bonds that were present in the first place or resulted from hydrogenation to those containing internal double bonds over a catalyst comprising at least one metal of the eighth transition group of the Periodic Table, in the presence of at least one added sulfur compound which contains at least 4 carbon atoms, and of hydrogen
c) separation of the sulfur compounds from the product mixture
d) optional recycling of the sulfur compounds separated from the product into the reactant stream
e) optional fractional processing of the virtually sulfur-free olefins.

Steps a) and b) can be carried out together or separately (in separate apparatus).

THE BRIEF DESCRIPTION OF DRAWINGS

A special embodiment of the invention is a process for the preparation of both a $C_4$-hydrocarbon mixture which comprises 2-butene as the only olefin, and a mixture which comprises isobutene and possibly 1-butene as olefins, from a $C_4$-cut comprising a maximum of 2% of dienes, which comprises the following steps:
a) Selective hydrogenation of the diene content from a maximum of 2% to below 5 ppm and simultaneous isomerization from 1-butene to give 2-butenes over a catalyst comprising at least one metal of the eighth transition group of the Periodic Table, in the presence of an added sulfur compound containing at least 4 carbon atoms which does not react with the olefins and has a higher boiling point than the product olefins.
b) Distillative separation of the reaction mixture, to give a top fraction comprising isobutene, isobutane and possibly 1-butene, a bottom fraction comprising the sulfur compounds, and a further fraction, which is withdrawn as a side stream from the lower part of the column, with 2-butenes and butane.
c) Recycling of a portion of the bottom fraction comprising the sulfur compounds into the reactor.

Figure 1:
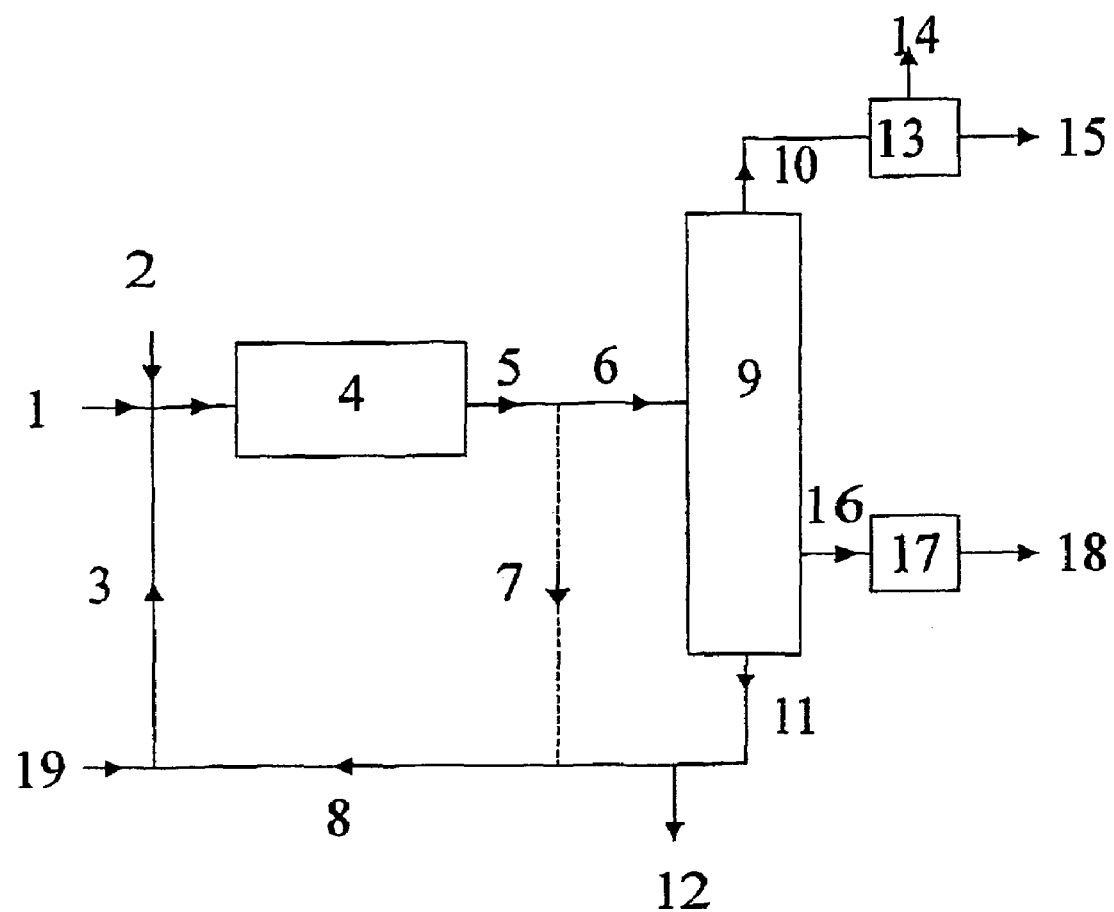
FIG. 1 is a block diagram of one embodiment of a plant for the hydroisomerization of $C_{4-6}$ olefins.

The process of the invention can be operated batchwise or advantageously continuously. Various process variants are possible for continuous operation. FIG. 1 shows as an example the block diagram of a plant in which the process for the processing of $C_4$-mixtures can be operated continuously. Reactant 1, hydrogen 2 and flow 3 comprising the sulfur compounds are fed into the hydrogenation and isomerization reactor 4. The reactor effluent 5 is partially or completely passed into the distillation column 9. An optionally removed portion of the reactor effluent 5 is passed back into the reactor 4 as stream 7. The top product 10 of column 9, which contains the total isobutene quantity, is condensed in the heat exchanger 13. After removal of the off-gas 14, a portion of the condensate is returned to the top of the column 9 as a reflux through a pipe not shown in the diagram. The other portion can be used in known applications. The 2-butene-containing fraction 16 is recovered in gaseous form as a side stream in the lower part of the column 9. It can be used directly or after condensation in heat exchanger 17. The bottom product 11 comprises sulfur compounds. This can be returned to the reactor 4, optionally after discharge of a bleed stream 12 from the system and replacement by fresh sulfur compounds 19.

Figure 2:
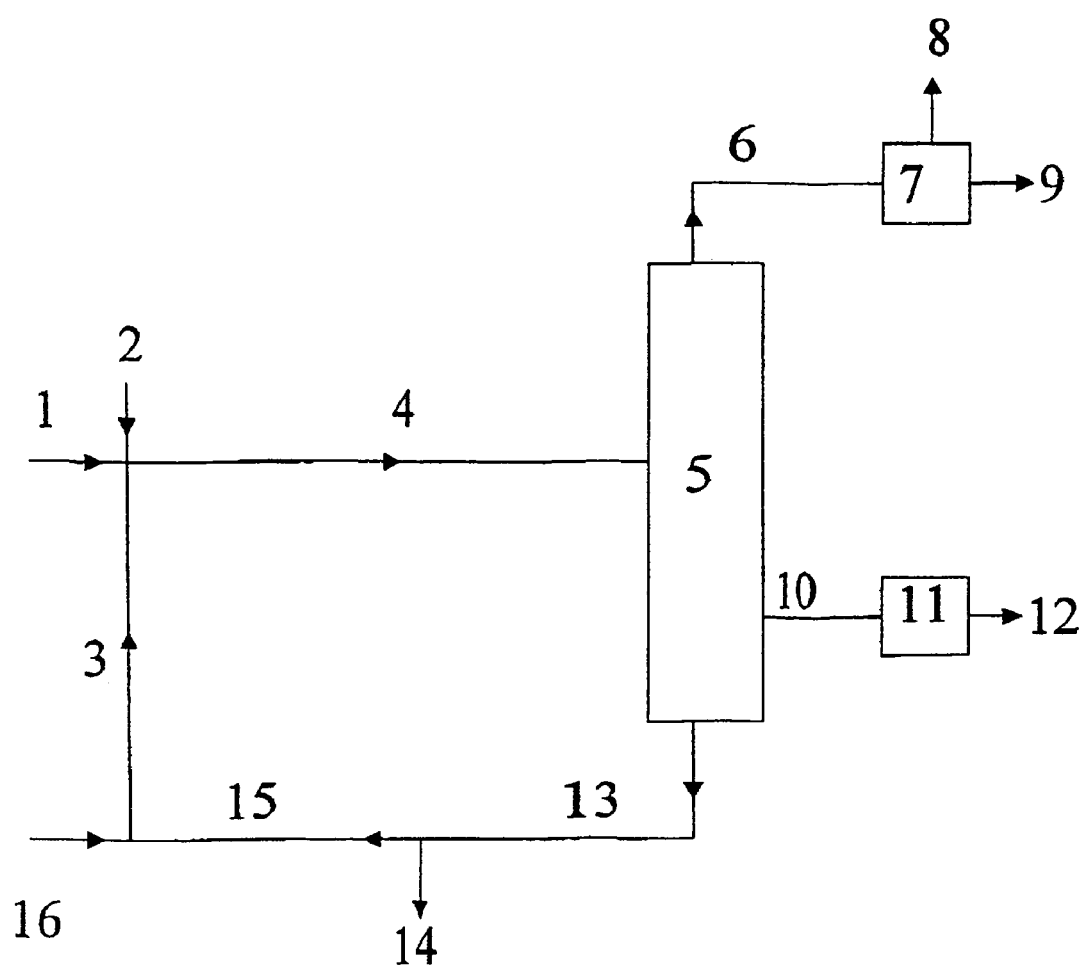
FIG. 2 is a block diagram of one embodiment of a plant for the hydroisomerization of $C_{4-6}$ olefins.

An alternative, second continuous process variant for the operation of the process according to the invention is shown in a block diagram in FIG. 2. Reactant 1, hydrogen 2 and sulfur compounds 3 are fed into a reactive column 5. This column contains a fabric packing comprising the catalyst. Hydrogenation, isomerization and fractionation are carried out simultaneously therein. An isobutene fraction is obtained as top product 6, which can be virtually free of 1-butene. After condensation in the heat exchanger 7, removal of off-gas 8, reflux of a portion to the top of the column 5 (reflux pipe not shown), flow 9 is obtained, which is used in downstream plants. The 2-butenefraction 10 (2-butene, n-butane) is recovered in gaseous form as a side stream in the lower part of the reaction column 5. This stream can, optionally after condensation in the heat exchanger 11, be subjected to further processing. The bottom product 13 comprises the sulfur compounds. This can be fed back into the reactor 5, optionally after discharge of a bleed stream 14 and replacement by fresh sulfur compounds 16.

The block diagram of a third continuous process variant for the operation of the process according to the invention only differs from FIG. 1 in that the apparatus 9 is a reactive distillation column.

According to the invention, the process is used for the removal of polyunsaturated hydrocarbons, in particular of dienes, and isomerization of olefins, in particular in hydrocarbon mixtures. Suitable feedstocks include olefin cuts which contain less than 5%, preferably less than 2%, of polyunsaturated compounds.

For the preparation of $C_5$- and $C_6$-olefins, light petroleum fractions from refineries and crackers are particularly useful. Industrial feedstocks for the recovery of $C_4$-olefins according to the process of the invention are low sulfur or sulfur-free $C_4$-cuts, such as raffinate I, which is recovered from the $C_4$-cut of a steam cracker by butadiene extraction, and hydrogenated steam cracker $C_4$-cut wherein the majority of the butadiene has been selectively hydrogenated to give linear butenes. Further useful reactants are olefin mixtures which have been obtained by Fischer-Tropsch synthesis. Furthermore, $C_4$-olefin mixtures which have been prepared by dehydrogenation of butanes or by other industrial processes, can be used. $C_4$-cuts from FCC units are generally sulfur-rich. These can only be used in the process of the invention if they have an untypically low sulfur content or if they have been partially or completely desulfurized. It is even possible to use more or less pure monoolefins.

According to the invention, crude materials are used that comprise less than 100 ppm, preferably less than 20 ppm of sulfur. Sulfur-rich feedstocks must therefore be subjected to at least a partial desulfurization before hydroisomerization. Furthermore, the sulfur compounds introduced with the feedstock, or the materials formed from them during hydrogenation and hydroisomerization, must be separable from the product. If their separation is carried out by distillation, they must have a different boiling point than the reactant olefins and target products.

Supported catalysts are used in the process of the invention which comprise at least one metal of the eighth transition group of the Periodic Table. A preferred metal is palladium. The metal concentrations are in the range from 0.2 to 2.0% (based on the complete catalyst), preferably from 0.5 to 1.0%. Useful support materials include MgO, $Al_2O_3$, $SiO_2$, $TiO_2$, $SiO_2/Al_2O_3$, $CaCO_3$ or activated carbon. Preferred support materials are $Al_2O_3$, $SiO_2$ and $SiO_2/Al_2O_3$.

The delivered fresh catalyst usually contains the active components in oxide or salt form. Reduction of the catalyst must therefore be carried before use using hydrogen or hydrogenous gas mixtures. The reduction of unreduced catalyst can take place in a separate reactor or in the hydroisomerization reactor. The active component is reduced to the metallic state in the process.

The catalyst can also be delivered and used in prereduced form.

The reduced catalyst catalyzes both the isomerization of the monoenes and the hydrogenation of the polyunsaturated hydrocarbons. Its activity must be lowered to such an extent that the isomerization of the monoolefins and the hydrogenation of the polyunsaturated hydrocarbons still occurs, yet the hydrogenation of the monoolefins is largely suppressed. According to the invention, the activity of the catalyst, which has optionally been presulfurized during its preparation, can be decreased and adjusted by means of sulfur compounds, in particular certain thioethers. The sulfur compounds, in particular the thioethers, are reversibly adsorbed on the catalyst. Their concentration on the catalyst surface is a function of the concentration of the sulfur compound in the reactor feed. The coating of the fresh catalyst by the sulfur compounds is carried out by charging the catalyst with a solution consisting of the sulfur compound and a solvent inert to the catalyst until the concentrations of the sulfur compound in the reactor feed and exit stream are equal. This allows uniform coating of the catalyst throughout the entire catalyst quantity. Useful solvents include, for example, hydrocarbons. It is convenient to use the material to be hydrogenated itself for this purpose.

According to the invention, the sulfur content in the reactor feed is in the range from 1 to 100 ppm, preferably from 2 to 20 ppm, during the reaction for controlling the catalyst activity and selectivity. The sulfur compounds used for this purpose must be soluble in the product and the reactant, bind reversibly to the catalyst and form no materials that poison the catalyst. Since products having very low sulfur contents are obtained by the process of the invention, the added sulfur compounds and sulfur compounds resulting therefrom must be removable by distillation.

It is known that most organic sulfur compounds are unstable under hydrogenating conditions, because a C—S or S—S bond is attacked. For example, hydrocarbons and hydrogen sulfides can be formed from mercaptans and mercaptans can be formed from dialkyl disulfides. The added sulfur compounds and the sulfur compounds formed therefrom can react with each other or with olefins, so that sulfurous materials having the same boiling range as the target products can be formed. A further disadvantage is that, formally, transalkylations can take place at the sulfur atom.

Furthermore, it is known that some sulfur compounds form azeotropes with hydrocarbons. For example, an azeotrope consisting of isobutane and methyl mercaptan having a boiling point of −13° C. is known (F. R. Brooks, A. C. Nixon, Journal of the American Chemical Society 1953, 75, 480).

The difficulties described dictate that, in the process of the invention, only selected sulfur compounds are suitable for the control of the catalyst activity.

The process of the invention employs sulfur compounds which can be regarded as inert under the reaction conditions and remain in the bottom product during working by distillation, and so can be removed by distillation. It was found according to the invention that certain thioethers having at least 4 carbon atoms fulfill these conditions. Both carbon groups of the thioethers found to be suitable can be identical or different as well as acyclic, cyclic, heterocyclic or aromatic. It is also possible for the compound employed to have more than one thioether group. All thioethers having at least 4 carbon atoms have a higher boiling point than the highest boiling monoolefin having 4 to 6 carbon atoms. These compounds can be separated from the product by distillation and are obtained as a bottom product.

In order to minimize the difficulty of distillative removal of the sulfur compounds, thioethers having a total of at least 8 carbon atoms are preferably used. The hydroisomerization of a $C_4$-cut is preferably carried out in the presence of dibutyl sulfides, in particular di-n-butyl sulfide. These allow the catalyst activity to be particularly well controlled. Furthermore, any transalkylations that occur on the sulfur atom will again lead to the formation of butyl thidethers, so that their effectiveness remains virtually constant and there is therefore no effect on the distillation, facilitating reaction control.

A mixture of two or more thioethers can optionally be used to control the hydroisomerization.

The reaction over the catalyst is carried out in the presence of hydrogen. The hydrogen quantity depends on the quantity of polyunsaturated hydrocarbons, in particular dienes, in the reactor feed. The quantity of hydrogen is 1 to 4 times, in particular 1 to 3 times, very particularly preferred 2.0 to 2.6 times, the stoichiometric quantity necessary for hydrogenation of the polyunsaturated hydrocarbons to give monoolefins. This applies to the concentration range of from 0.1 to 5 mass % of polyunsaturated hydrocarbons in the reactor feed.

In the concentration range of from 0 to 0.1 mass % of polyunsaturated hydrocarbons, the quantity of hydrogen metered in is based on the content of monoolefins in the reactor feed. In this concentration range, from 0.002 to 0.006 mol, in particular from 0.003 to 0.004 mol of hydrogen is metered in per mole of monoolefin.

The reaction is carried out in a temperature range of 30-150° C., in particular 40-120° C., very particularly preferably 80-100° C. The relatively low temperatures are particularly advantageous, since they allow a convenient thermodynamic equilibrium between olefins having internal double bonds and those having terminal double bonds. For example, the ratio of 2-butenes to 1-butene at thermodynamic equilibrium in this temperature range is from about 18:1 to 16:1.

In view of the low boiling points of the $C_4$-$C_6$-hydrocarbons, the reaction is preferably carried out under pressure, so that the reaction substantially takes place in the liquid phase. The pressure range is from 5 to 50 bar, preferably from 10 to 30 bar (absolute).

The reactions (isomerization or hydrogenation with isomerization) can be carried out by differing process variants. They can be carried out adiabatically or virtually isothermally, i.e. over a temperature rise of typically smaller than 10 K, and in one or more steps. In the latter case, all reactors, most conveniently tubular reactors, can be operated adiabatically or virtually isothermally, or some can be operated adiabatically and the others virtually isothermally. Furthermore, it is possible to convert the reactant in straight pass or with product recycling. The reactors can be operated as cocurrent reactors having trickle beds, preferably with high liquid space velocities. In the interests of a high space-time yield, reactors are preferably operated with high liquid space velocities in the range from 5 to 100 m$^3$, in particular from 15 to 30 m$^3$ per m$^2$ of cross section of the empty reactor per hour. When a reactor is operated isothermally and in straight pass, the liquid hourly space velocities can have values in the range from 1 to 20 h$^{-1}$, preferably 4 to 12 h$^{-1}$.

In order to avoid hot spots in the reactor, which can lead to damage of the catalyst and to the formation of by-products, it is convenient to limit the concentration of terminal olefins in the reactor feed to at most 20 mass %, in particular at most 15 mass %. When the content of terminal olefins in the reactant is above this limit, it is diluted. It is convenient to use the hydroisomerizate as the diluent.

The sulfur compounds are separated from the effluent of the hydroisomerization reactor. This is carried out, for example, by adsorption or preferably by distillation. The sulfur-free crude products obtained in this way can be further processed by known methods, for example alkylation to give low-sulfur gasoline components.

The distillative workup in one or more columns removes the sulfur compounds and preferably separates the olefins into at least two fractions.

In a preferred embodiment, for example, a C$_4$-hydroisomerization mixture is separated in only one column into a top, side and bottom fraction. The distillation pressure is in the range from 3 to 20 bar, in particular from 3 to 10 bar, very particularly from 6 to 8 bar (absolute). The average distillation temperature is in the range from 30 to 130° C., in particular from 30 to 100° C., very particularly preferably between 60 and 70° C. The reflux ratio is in the range from 5 to 30, in particular from 10 to 20 and very particularly preferably from 15 to 20.

The side stream withdrawal is carried out at a plate which is located from 1 to 15 theoretical plates above the bottom.

A further operating variant is to carry out the reaction (isomerization or hydrogenation and isomerization) and separation simultaneously in a column reactor which comprises internal fitments and catalyst. For example, when a C$_4$-cut is the reactant, a pressure of from 6 to 10 bar and a temperature of from 60 to 100° C. are used. This allows a virtually isobutene-free top product to be obtained.

Furthermore, it is possible to allow the majority of the conversions to take place in one or more reactors, and to carry out the remaining conversions together with the separation in a reactive distillation column.

Sulfur compounds remaining in the bottom product can be fed back into the reactor. A portion of the bottom product can be discharged from the system, in order to prevent an increase in the sulfur content through any sulfur compounds introduced with the reactant, or to remove sulfur compounds having undesirable properties from the process. Alternatively, sulfur compounds having defined properties can be added to the recycling stream. The possibility therefore exists to control the catalyst activity through the sulfur content and the type of sulfur compounds in the reactor feed.

Only when the reactant is free from high-boilers, and no high-boilers are formed during hydroisomerization or hydrogenation and hydroisomerization, can the sulfur compounds be recycled in their entirety. However, if high-boilers, with the exception of sulfur compounds, are obtained in the distillation bottom, sulfur compounds are discharged together with the high-boilers, so that sulfur recycling is not economically viable. For example, when a sulfur-free C$_4$-hydrocarbon stream comprising 1 mass % of high-boilers (hydrocarbons having more than 4 carbon atoms) is hydroisomerized or hydrogenated and hydroisomerized in accordance with the invention while keeping the content of high-boilers in the hydroisomerization reactor below 5 mass %, about 20% of the added sulfur compounds are discharged with the high-boilers.

The degree of recycling of the sulfur compounds can therefore vary in the range of from 100 to 10%, depending upon the composition of the reactant among other factors. Typically, it is in the range from 100 to 50%, in particular from 95 to 60%, during the hydroisomerization or hydrogenation and hydroisomerization of C$_4$-hydrocarbon mixtures.

When the bottom fraction is a mixture of sulfur compounds, high-boilers, product and/or reactant, it is convenient to separate reactants and products from the high-boilers to be discharged in a further distillation.

When a C$_4$-cut is hydroisomerized or hydrogenated and hydroisomerized, and processed by distillation, a top product is obtained that comprises isobutene, 1-butene and isobutane, and a maximum of 1 mass-ppm, in particular 500 mass-ppb, very particularly 100 mass-ppb of sulfur. This mixture can be separated in a further column to give isobutane and olefins. The olefinic mixture can be used in known processes, for example in the preparation of MTBE. When the hydroisomerization is carried out in a column reactor, a virtually 1-butene-free isobutene can be obtained. This can be used in reactions which are upset by 1-butene.

The 2-butenes, which comprise butane, are withdrawn in gaseous form as a side stream. The sulfur content is below 500 mass-ppb, in particular below 100 mass-ppb, very particularly below 50 mass-ppb and is then particularly suitable for the preparation of gasoline alkylate. After removal of these sulfur traces, for example by adsorption on a fixed bed absorbent, for example a molecular sieve, the 2-butene mixture can be used for extremely sulfur-sensitive chemical reactions such as oligomerization over nickel catalysts.

The process of the invention thus has the following particular advantages:

Polyunsaturated hydrocarbons are hydrogenated to a content of below 5 ppm.

Even at high monoene concentrations in the reactant, only small, if any, losses of monoolefin through over-hydrogenation occur.

The isomer ratio of the monoolefins is close to the thermodynamic equilibrium.

The olefins recovered or their mixtures can advantageously be used for the preparation of low-sulfur products.

The sulfur component is almost completely recovered and therefore results in only low costs.

The activity of the catalyst can be adjusted to operating needs.

The examples which follow illustrate the invention.

The concentrations given in the examples are obtained by the use of the following analytical methods:

Determination of the C$_4$-isomers:

| Gas chromatographic investigation (100% normalization) | |
|---|---|
| Detector: | FID |
| Column: | 50 m PLOT Al$_2$O$_3$/Na$_2$SO$_4$; 0.32 mm ID; 5 µm film thickness (Chrompack) |
| Oven temperature: | 125° C. isothermal |
| Detector temperature: | 140° C. |
| Injector temperature: | 200° C. |

-continued

| Gas chromatographic investigation (100% normalization) | |
|---|---|
| Carrier gas: | helium 3.0 ± 0.5 ml/min |
| Pre-column pressure: | 180 ± 10 kPa |
| Split: | 200 ± 20 ml/min |
| Injection quantity: | 50 µl |

The determination of 1,3-butadiene in the trace region (detection limit: 5 mg/kg) is carried out in the same way as the determination of the $C_4$-isomers, except with an injection quantity of 1.0 ml.

Determination of the sulfur in the trace region (detection limit: 5-10 µg/kg):

| Gas chromatographic investigation (external standard method) | |
|---|---|
| Detector: | FPD |
| Column: | 25 m CP-SIL 5 CB; 0.53 mm ID; 5 µm film thickness (Chrompack) |
| Oven temperature: | 35° C.; 1 min; 20 K/min; 190° C.; 9 min |
| Detector temperature: | 160° C. |
| Injector temperature: | 180° C. |
| Carrier gas: | helium 15.0 ± 2.0 ml/min |
| Pre-column pressure: Splitless | 60 ± 10 kPa |
| Injection quantity: | 5 µl (liquid, condensed at −80° C.) |

EXAMPLE 1

Comparative

The hydroisomerization of a $C_4$ crude material is carried out in liquid phase over a fixed bed catalyst which comprises 1% palladium on $Al_2O_3$ and was prepared similarly to a method in EP-A-0 636 667. The crude material is pre-heated to 55° C. and introduced adiabatically to the reactor in straight pass. The reaction takes place at an average temperature of 80° C. The liquid hourly space velocity (LHSV, volume of reactant per volume of catalyst per unit time) is 12 l/(l*h), and the molar hydrogen/diene ratio 2.0. The crude material contains no sulfur. Table 1 shows the composition of the reactor feed and effluent.

TABLE 1

| Component (mass %) | Feed (mass %) | Effluent (mass %) |
|---|---|---|
| 1,3-Butadiene | 0.4 | 0 |
| Isobutene | 25.2 | 25.2 |
| 1-Butene | 38.2 | 5.6 |
| 2-Butenes | 26.7 | 58.4 |
| Isobutane | 3.2 | 3.2 |
| n-Butane | 7.0 | 7.6 |

EXAMPLE 2

Comparative

The hydroisomerization is carried out as described in Example 1, except that sulfur in the form of dimethyl disulfide is added to the crude material in such an amount that the sulfur concentration in the reactor feed is 3 ppm. Table 2 shows the composition of the reactor effluent. Analysis of the sulfur components in the product shows a mixture of different sulfur compounds. As well some unidentified components, dimethyl disulfide, methyl butyl sulfide and dibutyl sulfide are shown to be present. The concentrations of sulfur are in the range from 20 to 700 ppb. The sulfur compounds cannot be removed by distillation (as described in Examples 4 and 5).

TABLE 2

| Component (mass %) | Effluent (mass %) |
|---|---|
| 1,3-Butadiene | 0 |
| Isobutene | 25.2 |
| 1-Butene | 3.4 |
| 2-Butenes | 60.7 |
| Isobutane | 3.2 |
| n-Butane | 7.5 |

This example clearly shows the benefit of sulfur addition for hydroisomerization, but also shows the difficulties associated with the removal of the sulfur compounds.

EXAMPLE 3

Inventive

The hydroisomerization is carried out as described in Example 1, except that sulfur in the form of di-n-butyl sulfide is added to the crude material in such an amount that the sulfur concentration in the reactor feed is 3 ppm. Table 3 shows the composition of the reactor effluent. Analysis of the sulfur components in the product shows that only one sulfur component is present, namely di-n-butyl sulfide. The concentrations of this sulfur component in the feed and effluent are identical.

TABLE 3

| Component (Ma %) | Effluent (Ma %) |
|---|---|
| 1,3-Butadiene | 0 |
| Isobutene | 25.2 |
| 1-Butene | 3.3 |
| 2-Butenes | 60.9 |
| Isobutane | 3.2 |
| n-Butane | 7.4 |

This example documents the advantageous use of the sulfur component in the form of di-n-butyl sulfide, which is not converted to other sulfur components in the reactor and can be separated from the $C_4$-cut by distillation (see Examples 4 and 5).

EXAMPLE 4

Inventive Separation and Recycling of the Sulfur Compound

The reactor effluent from Example 3 is separated by distillation. The task of firstly separating isobutene from the 2-butenes and secondly recovering the 2-butenes obtained as high-boilers in a sulfur-free form, is carried out as follows:

The reactor effluent is fed in to the upper third (plate 45 from top) of a distillation column having about 150 theoretical plates. The isobutene fraction is withdrawn at the top of the column, condensed and partially returned to the top of the column (reflux). A 2-butene-rich product flow is withdrawn in vaporous form from a stripping section of the column (withdrawal plate: about plate 1 to 15 from the bottom) and condensed outside the column. The high-boiling sulfur component accumulates in the bottom product of the column. The bottom product can (after removal of any high-boiling hydrocarbons) be returned to the feed of the hydroisomerization reactor according to the invention, so that a closed sulfur circuit results.

Distillation conditions:

| | |
|---|---|
| Number of theoretical plates: | 150 |
| Column diameter: | 200 mm |
| Top of column pressure: | 6 bar |
| Base of column temperature: | 68° C. |
| Top of column temperature: | 49° C. |
| Reflux ratio: | 16 |
| Feed rate: | 5000 g/h |
| Bottom product withdrawal: | †g/h |
| Distillate rate: | 1636 g/h |
| Side stream withdrawal: | 3318 g/h |

Table 4 shows the compositions of the different streams during the distillation.

TABLE 4

| Component | Feed | Distillate | Bottom | Side stream |
|---|---|---|---|---|
| Isobutene (Ma %) | 25.2 | 76.8 | 0.04 | 0.2 |
| 1-Butene (Ma %) | 3.3 | 10.0 | —/— | 0.05 |
| 2-Butenes (Ma %) | 60.9 | 0.6 | 83.7 | 90.1 |
| Isobutane (Ma %) | 3.2 | 9.8 | —/— | —/— |
| n-Butane (Ma %) | 7.4 | 2.8 | 4.6 | 9.7 |
| S (ppm) | 3 | —/— | 322 | —/— |

—/— not quantifiable, sulfur is present as di-n-butyl sulfide

This example documents that the sulfur compounds can be efficiently removed, so that virtually sulfur-free products can be recovered.

EXAMPLE 5

Inventive Separation and Recycling of the Sulfur Compounds

Although a sulfur concentration of 3 ppm in the feed was found to be sufficient for the hydroisomerization, this example is carried out at a sulfur concentration of 20 ppm in the feed to the column, in order to improve the performance of this method of sulfur separation. Apart from the sulfur content, the composition of the column feed corresponds to that for Example 4. The distillation apparatus and conditions are the same as in Example 4.

TABLE 5

Composition of the different streams during the distillation

| Component | Feed | Distillate | Bottom | Side Stream |
|---|---|---|---|---|
| Isobutene (Ma %) | 25.2 | 76.8 | 0.04 | 0.2 |
| 1-Butene (Ma %) | 3.3 | 10.0 | —/— | 0.05 |
| 2-Butenes (Ma %) | 60.9 | 0.6 | 83.7 | 90.1 |
| Isobutane (Ma %) | 3.2 | 9.8 | —/— | —/— |

TABLE 5-continued

Composition of the different streams during the distillation

| Component | Feed | Distillate | Bottom | Side Stream |
|---|---|---|---|---|
| n-Butane (Ma %) | 7.4 | 2.8 | 4.6 | 9.7 |
| S (ppm) | 20 | 0.006 | 2152 | 0.03 |

Sulfur is present in the form of di-n-butyl sulfide

This example shows that products having low sulfur concentrations are obtainable even when comparatively high sulfur concentrations are present in the column feed.

What is claimed is:

1. A process for the hydroisomerization of $C_4$-$C_6$-olefins, comprising:
hydroisomerizing a hydrocarbon feed which is (1) a mixture of $C_4$-$C_6$-olefins or (2) an olefinic cut containing $C_4$-$C_6$-olefins, said feed containing from 0.1 to 5% of polyunsaturated hydrocarbons, the mixtures (1) and (2) containing only sulfur compounds that can be separated from the mixed olefin product obtained by distillation or which on hydroisomerization give rise to sulfurous compounds which can be separated from the olefins by distillation, wherein the mixtures of $C_4$-$C_6$-olefins or the olefinic cut contains olefins having terminal double bonds which are hydroisomerized to olefins that contain internal double bonds and wherein the polyunsaturated hydrocarbons in the hydrocarbon feed are simultaneously hydrogenated to monoolefins with an amount of hydrogen ranging from 1 to 4 times the stoichiometric quantity of hydrogen required to selectively hydrogenate the polyunsaturated hydrocarbons to the corresponding monoolefins, over a catalyst comprising an element of the eighth transition group of the Periodic Table in the presence of at least one added sulfur compound which contains at least 4 carbon atoms, thereby producing a mixed $C_4$-$C_6$-olefin product in which the quantitative ratio of the $C_4$-$C_6$-olefins containing internal double bonds to the $C_4$-$C_6$-olefins containing terminal double bonds is at its thermodynamic equilibrium value at a reaction temperature ranging from 30 to 150° C., which in the case of the ratio of 2-butene to 1-butene ranges from 18:1 to 16:1.

2. The process according to claim 1, wherein said catalyst is a supported catalyst which comprises from 0.2 to 2.0% palladium, based on the total weight of the supported catalyst.

3. The process according to claim 1, wherein aluminum oxide ($Al_2O_3$), silicon dioxide ($SiO_2$) or silica-aluminum oxide ($SiO_2/Al_2O_3$) is the catalyst support.

4. The process according to claim 1, wherein the sulfur content in the hydrocarbon feed is in the range from 1 to 100 ppm.

5. The process according to claim 1, wherein the sulfur compound is a thioether which is introduced into the hydrocarbon feed.

6. The process according to claim 5, wherein the thioether has at least 8 carbon atoms.

7. The process according to claim 6, wherein said thioether is dibutyl sulfide.

8. The process according to claim 1, wherein hydrogen in an amount ranging from 2 to 2.6 times the stoichiometric quantity of hydrogen required to selectively hydrogenate the polyunsaturated hydrocarbons to give the corresponding monoolefins is present for the hydrogenation reaction when a concentration ranging from 0.1 to 5 mass % of polyunsaturated hydrocarbons is present in the hydrocarbon feed.

9. The process according to claim 1, wherein the hydroisomerization effluent is separated into at least one olefin fraction and a fraction which comprises the sulfur compounds.

10. The process according to claim 1, wherein a portion of the sulfur compounds separated by distillation is fed into the hydrocarbon feed.

11. The process according to claim 1, wherein the mixed $C_4$-$C_6$-olefin product is separated into a sulfurous fraction and at least two olefinic fractions.

12. The process according to claim 11, wherein the fractionation is conducted in a single distillation column.

13. The process according to claim 11, wherein the fractionation is conducted in at least two distillation columns.

14. The process according to claim 11, wherein a $C_4$-olefin product is separated into a low-boiler fraction comprising isobutene, optionally 1-butene, and isobutane, a middle fraction comprising 2-butenes and optionally n-butane and a high-boiler fraction comprising sulfur compounds.

15. The process according to claim 14, wherein the side stream is withdrawn from a plate located from 1 to 15 theoretical plates above the bottom.

16. The process according to claim 11, wherein a $C_4$-olefin product is separated in a column into a top fraction, which comprises isobutene, optionally 1-butene, and isobutane, a side stream comprising 2-butenes and optionally n-butane, and a high-boiler fraction comprising sulfur compounds.

17. The process according to claim 16, wherein the side stream is withdrawn in vaporous form.

18. The process according to claim 1, wherein the sulfur content of the olefin fraction is smaller than 500 ppb.

* * * * *